US012029518B2

(12) United States Patent
Tanaka et al.

(10) Patent No.: US 12,029,518 B2
(45) Date of Patent: Jul. 9, 2024

(54) METHOD OF CONTROLLING SURGICAL SYSTEM AND SURGICAL SYSTEM

(71) Applicant: KAWASAKI JUKOGYO KABUSHIKI KAISHA, Kobe (JP)

(72) Inventors: Hideki Tanaka, Kobe (JP); Toshiyuki Homma, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 554 days.

(21) Appl. No.: 17/436,953

(22) PCT Filed: Mar. 4, 2020

(86) PCT No.: PCT/JP2020/009097
§ 371 (c)(1),
(2) Date: Sep. 7, 2021

(87) PCT Pub. No.: WO2020/179815
PCT Pub. Date: Sep. 10, 2020

(65) Prior Publication Data
US 2022/0168057 A1 Jun. 2, 2022

(30) Foreign Application Priority Data
Mar. 6, 2019 (JP) ................................ 2019-040196

(51) Int. Cl.
*A61B 1/05* (2006.01)
*A61B 1/00* (2006.01)
(Continued)

(52) U.S. Cl.
CPC .......... *A61B 34/70* (2016.02); *A61B 1/00149* (2013.01); *A61B 1/0051* (2013.01);
(Continued)

(58) Field of Classification Search
CPC ..... A61B 1/00149; A61B 34/70; A61B 90/37; A61B 34/37; A61B 1/0051; A61B 34/30;
(Continued)

(56) References Cited

U.S. PATENT DOCUMENTS 8,792,963 B2 * 7/2014 Zhao ...................... A61B 34/20
382/128
9,931,025 B1 * 4/2018 Graetzel ............ A61B 1/00006
(Continued)

FOREIGN PATENT DOCUMENTS

EP       2 263 590 A2    12/2010
JP       H08-196541 A     8/1996
(Continued)

OTHER PUBLICATIONS

Dai et al., An endoscope holder with automatic tracking feature for nasal surgery, 2016, IEEE, p. 1-6 (Year: 2016).*
(Continued)

*Primary Examiner* — Mcdieunel Marc
(74) *Attorney, Agent, or Firm* — Oliff PLC

(57) ABSTRACT

To easily acquire an image of a tip end portion of a surgical instrument attached to a manipulator arm even when the surgical instrument is bent, a surgical system includes manipulator arms, a manipulation unit, and a controller. The manipulator arms include: a first manipulator arm including an instrument holder holding a first surgical instrument including an instrument bendable portion; and a second manipulator arm including an instrument holder holding an endoscope assembly including an endoscope bendable portion and a camera at a tip end portion of the endoscope assembly. A method of controlling the surgical system controls the endoscope assembly such that the endoscope assembly is bent so as to follow bending of the first surgical instrument that is bent based on an operating command.

14 Claims, 4 Drawing Sheets

(51) Int. Cl.
  *A61B 1/005* (2006.01)
  *A61B 34/00* (2016.01)
  *A61B 34/37* (2016.01)
  *A61B 34/30* (2016.01)

(52) U.S. Cl.
  CPC ............... *A61B 1/05* (2013.01); *A61B 34/37* (2016.02); *A61B 2034/301* (2016.02)

(58) Field of Classification Search
  CPC ... A61B 90/361; A61B 1/05; A61B 2034/301; A61B 2017/00314; A61B 2034/302; A61B 2034/306; A61B 2090/373
  See application file for complete search history.

(56) References Cited

U.S. PATENT DOCUMENTS

| | | | | |
|---|---|---|---|---|
| 10,952,801 | B2* | 3/2021 | Miller | B25J 9/1638 |
| 11,653,987 | B2* | 5/2023 | Miller | B25J 9/1638 606/1 |
| 11,969,217 | B2* | 4/2024 | Rafii-Tari | A61B 90/37 |
| 2012/0020547 | A1* | 1/2012 | Zhao | G16H 30/40 382/153 |
| 2017/0079730 | A1 | 3/2017 | Azizian et al. | |
| 2017/0172676 | A1 | 6/2017 | Itkowitz et al. | |
| 2020/0261169 | A1* | 8/2020 | Miller | B25J 9/1607 |
| 2021/0354286 | A1* | 11/2021 | DiMaio | A61B 34/76 |
| 2024/0138934 | A1* | 5/2024 | Defonzo | A61B 34/30 |

FOREIGN PATENT DOCUMENTS

| | | |
|---|---|---|
| JP | 2013-220107 A | 10/2013 |
| JP | 2017-513550 A | 6/2017 |
| JP | 2017-515524 A | 6/2017 |
| WO | 2019/040278 A1 | 2/2019 |

OTHER PUBLICATIONS

Bardou et al., Design of a telemanipulated system for transluminal surgery, 2009, IEEE, p. 5577-5582 (Year: 2009).*
Staub et al., Autonomous High Precision Positioning of Surgical Instruments in Robot-Assisted Minimally Invasive Surgery under Visual Guidance, 2010, IEEE, p. 64-69 (Year: 2010).*
Berkelman et al., Control and user interface design for compact manipulators in minimally-invasive surgery, 2005, IEEE, pg. (Year: 2005).*

* cited by examiner

METHOD OF CONTROLLING SURGICAL SYSTEM AND SURGICAL SYSTEM

CROSS-REFERENCE TO RELATED APPLICATIONS

This is a National Phase of International Application No. PCT/JP2020/009097 filed Mar. 4, 2020, which claims the benefit of Japanese Application No. 2019-040196 filed Mar. 6, 2019. The disclosure of the prior application is hereby incorporated by reference herein in its entirety.

TECHNICAL FIELD

The present disclosure relates to a method of controlling a surgical system and the surgical system.

BACKGROUND ART

Known is a master-slave system which includes manipulator arms and performs surgery by moving the manipulator arms based on manipulation of an operator (see PTLs 1 and 2, for example). In such system, various surgical instruments, such as a forceps unit, are attached to tip end portions of the manipulator arms. One example of the surgical instruments attached to such system is a surgical instrument which includes a bendable portion and is bendable relative to a longitudinal direction extending from a base end portion of the surgical instrument to a tip end portion of the surgical instrument (see PTL 3, for example).

CITATION LIST

Patent Literature

PTL 1: Published Japanese Translation of PCT Application No. 2017-515524
PTL 2: Published Japanese Translation of PCT Application No. 2017-513550
PTL 3: Japanese Laid-Open Patent Application Publication No. 2013-220107

SUMMARY OF INVENTION

Technical Problem

According to the above surgical system, an endoscope assembly including a camera at a tip end portion thereof is attached to one of the manipulators. While watching images taken by the camera of the endoscope assembly, the operator performs surgery by using the other manipulator arms.

Moreover, in the above surgical system, the manipulator arms are attached to a single arm base (also called a platform). Furthermore, for example, in laparoscopic surgery performed by using the surgical system, to reduce invasiveness at a surgical site of a patient, largely cutting an abdomen of the patient is not performed, but one or several openings are made at the abdomen of the patient. Then, the surgical instrument and the endoscope assembly are introduced into the body of the patient through the openings. To reduce the invasiveness at the surgical site of the patient, it is preferable that the number of openings be small.

Due to the above restriction, the tip end portions of the manipulator arms are directed in substantially the same direction. Therefore, typically, the image taken by the camera of the endoscope assembly shows parts located in a deeper direction of the tip end portion of the surgical instrument (i.e., a direction from the base end portion of the surgical instrument to the tip end portion of the surgical instrument).

However, when an instrument including a bendable portion is attached as the surgical instrument to the manipulator arm, the surgical instrument can take such position and posture that the tip end portion of the surgical instrument is directed toward the base end of the manipulator arm. In this case, to appropriately take an image of the surgical site, it is desirable that the image taken by the camera of the endoscope assembly shows parts located in a shallower direction of the tip end portion of the surgical instrument. However, due to the above restriction, there is a limit to arrange the manipulator arm to which the endoscope assembly is attached, such that the endoscope assembly can take an image of parts located at a farther side (for example, the base end side of the surgical instrument) of the tip end portion of the surgical instrument that is bent.

Increasing the number of openings to realize the arrangement of the endoscope assembly leads to a burden on the patient. Moreover, it is troublesome for the operator to adjust the arrangement of the endoscope assembly when bending the surgical instrument.

The present disclosure was made to solve the above problems, and an object of the present disclosure is to provide a method of controlling a surgical system and the surgical system, each of which can easily acquire an image of a tip end portion of a surgical instrument attached to a manipulator arm even when the surgical instrument is bent.

Solution to Problem

One aspect of the present disclosure is a method of controlling a surgical system, the surgical system including: manipulator arms including respective instrument holders at tip end portions of the manipulator arms, the instrument holders holding respective long-axis surgical instruments, the tip end portions of the manipulator arms being three-dimensionally movable relative to corresponding base end portions of the manipulator arms; a manipulation unit that generates, based on a manipulation input, an operating command that moves the manipulator arms; and a controller that controls movements of the manipulator arms based on the operating command. The manipulator arms include a first manipulator arm including the instrument holder holding a first surgical instrument including an instrument bendable portion and a second manipulator arm including the instrument holder holding an endoscope assembly including an endoscope bendable portion and a camera at a tip end portion of the endoscope assembly. The method includes controlling the endoscope assembly such that the endoscope assembly is bent so as to follow bending of the first surgical instrument that is bent based on the operating command.

According to the above control method, the first surgical instrument and the endoscope assembly are bendable, and the endoscope assembly is controlled such that the endoscope assembly is bent so as to follow the bending of the first surgical instrument. Therefore, the direction of an image taken by the camera of the endoscope assembly is easily adjusted in accordance with the movement of the tip end portion of the first surgical instrument to a direction in which the tip end portion of the first surgical instrument is directed. Thus, even when the first surgical instrument is bent, the image of the tip end portion of the first surgical instrument can be easily acquired.

A bending angle of the endoscope bendable portion of the endoscope assembly may be determined in accordance with a bending angle of the instrument bendable portion of the first surgical instrument. According to this, the bending of the endoscope assembly can be made to follow the bending of the first surgical instrument by simple control.

The surgical system may include a storage that stores data readable by the controller. The storage may store a position and posture of a tip end portion of the first surgical instrument before the instrument bendable portion is bent and a position and posture of the tip end portion of the endoscope assembly before the endoscope bendable portion is bent. The method may include performing, when the first surgical instrument is bent, first calculation processing of determining the position and posture of the endoscope assembly such that a relative relation between the position and posture of the tip end portion of the first surgical instrument before the instrument bendable portion is bent and the position and posture of the tip end portion of the endoscope assembly before the endoscope bendable portion is bent is maintained. According to this, the bending operation of the first surgical instrument and the bending operation of the endoscope assembly are performed in a state where the relative relation between the position and posture of the tip end portion of the first surgical instrument and the position and posture of the tip end portion of the endoscope assembly is maintained. Therefore, the image region taken by the camera of the endoscope assembly for the tip end portion of the first surgical instrument is maintained before and after the bending. Thus, the adjustment of the endoscope assembly after the bending operation of the first surgical instrument can be reduced.

When the position of the endoscope assembly is undeterminable in the first calculation processing such that the relative relation is maintained, the posture of the tip end portion of the endoscope assembly may be determined such that a relation between the posture of the tip end portion of the first surgical instrument before the instrument bendable portion is bent and the posture of the tip end portion of the endoscope assembly before the endoscope bendable portion is bent is maintained. According to this, even when the relative relation between the position and posture of the tip end portion of the first surgical instrument and the position and posture of the tip end portion of the endoscope assembly cannot be maintained, the surgical system operates such that the relation between the posture of the tip end portion of the first surgical instrument and the posture of the tip end portion of the endoscope assembly is maintained. Therefore, the endoscope assembly can be made to follow the bending operation of the first surgical instrument as much as possible.

When the position of the endoscope assembly is undeterminable in the first calculation processing such that the relative relation is maintained, a bending angle of the endoscope bendable portion of the endoscope assembly may be determined in accordance with a bending angle of the instrument bendable portion of the first surgical instrument. According to this, even when the relative relation between the position and posture of the tip end portion of the first surgical instrument and the position and posture of the tip end portion of the endoscope assembly cannot be maintained, the bending angle of the endoscope bendable portion of the endoscope assembly is determined in accordance with the bending angle of the instrument bendable portion of the first surgical instrument. Therefore, the endoscope assembly can be made to follow the bending operation of the first surgical instrument as much as possible.

The first calculation processing may be performed based on a constraint condition that the bending angle of the endoscope bendable portion of the endoscope assembly corresponds to the bending angle of the instrument bendable portion of the first surgical instrument. With this, the calculation of the position and posture of the endoscope assembly based on the bending of the endoscope assembly can be performed, and the amount of calculation can be reduced.

The manipulator arms may include a third manipulator arm including the instrument holder holding a second surgical instrument including an instrument bendable portion. In the method, the endoscope assembly may be bendable so as to follow bending of the second surgical instrument that is bent based on the operating command. A surgical instrument to be followed by the endoscope assembly may be selectable from the first surgical instrument and the second surgical instrument. With this, when there are the plural manipulator arms to which the surgical instruments are attached, an image of a part that an operator wants to see can be easily acquired.

A surgical system according to another aspect of the present disclosure includes: manipulator arms including respective instrument holders at tip end portions of the manipulator arms, the instrument holders holding respective long-axis surgical instruments, the tip end portions of the manipulator arms being three-dimensionally movable relative to corresponding base end portions of the manipulator arms; a manipulation unit that generates, based on a manipulation input, an operating command that moves the manipulator arms; and a controller that controls movements of the manipulator arms based on the operating command. The manipulator arms include a first manipulator arm including the instrument holder holding a first surgical instrument including an instrument bendable portion and a second manipulator arm including the instrument holder holding an endoscope assembly including an endoscope bendable portion and a camera at a tip end portion of the endoscope assembly. The controller controls the endoscope assembly such that the endoscope assembly is bent so as to follow bending of the first surgical instrument that is bent based on the operating command.

According to the above configuration, the first surgical instrument and the endoscope assembly are bendable, and the endoscope assembly is controlled such that the endoscope assembly is bent so as to follow the bending of the first surgical instrument. Therefore, the direction of an image taken by the camera of the endoscope assembly is easily adjusted in accordance with the movement of the tip end portion of the first surgical instrument to a direction in which the tip end portion of the first surgical instrument is directed. Thus, even when the first surgical instrument is bent, the image of the tip end portion of the first surgical instrument can be easily acquired.

The above object, other objects, features, and advantages of the present disclosure will be made clear by the following detailed explanation of preferred embodiments with reference to the attached drawings.

Advantageous Effects of Invention

The present disclosure has an effect of being able to easily acquire an image of a tip end portion of a surgical instrument attached to a manipulator arm even when the surgical instrument is bent.

DESCRIPTION OF EMBODIMENTS

Hereinafter, an embodiment of the present disclosure will be described with reference to the drawings. However, the present disclosure is not limited to the present embodiment. Moreover, in the following description and the drawings, the same reference signs are used for the same or corresponding components, and the repetition of the same explanation is avoided.

Figure 1:
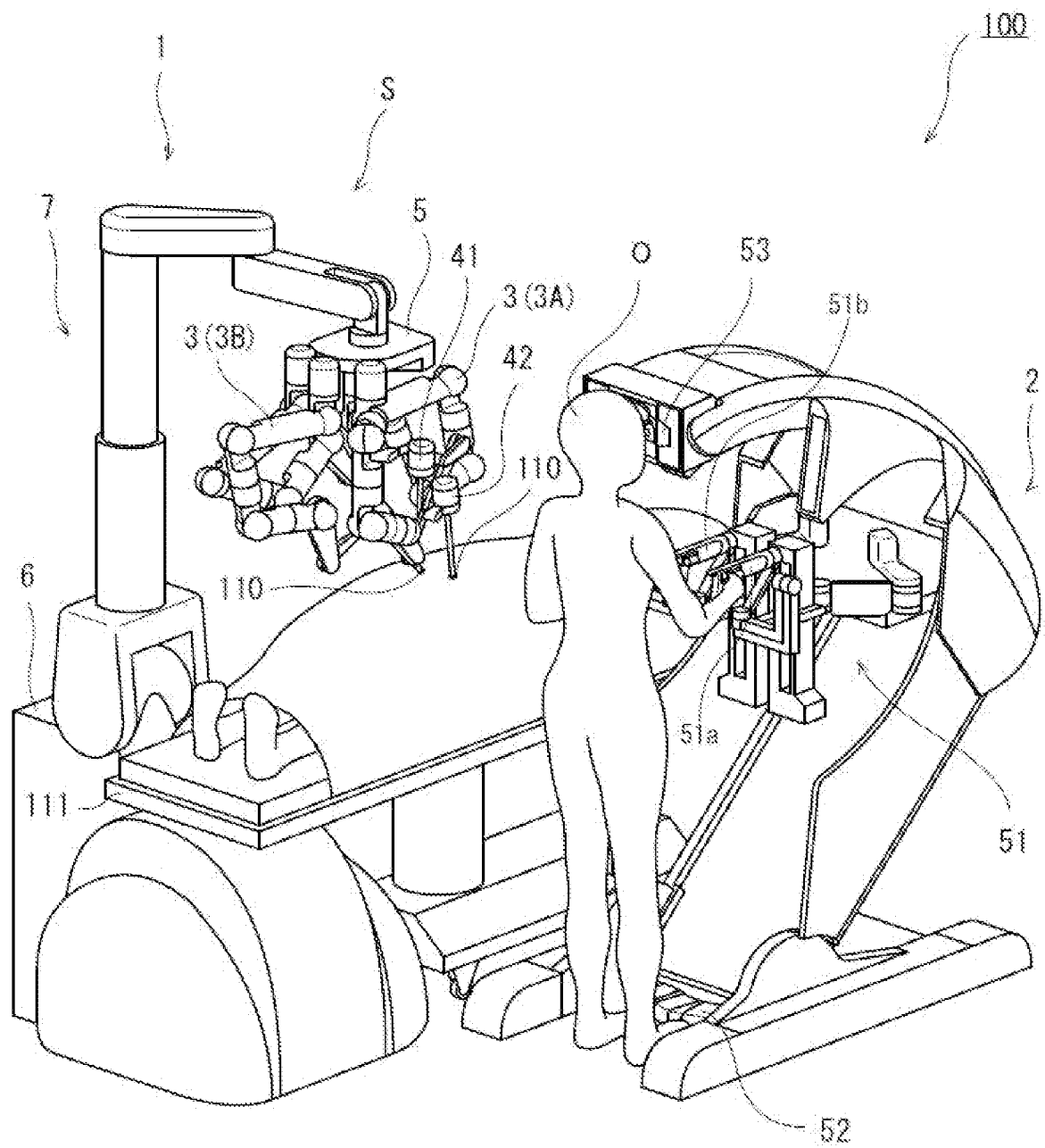
FIG. 1 is a schematic diagram showing an entire configuration of a surgical system according to one embodiment of the present disclosure.
Figure 2:
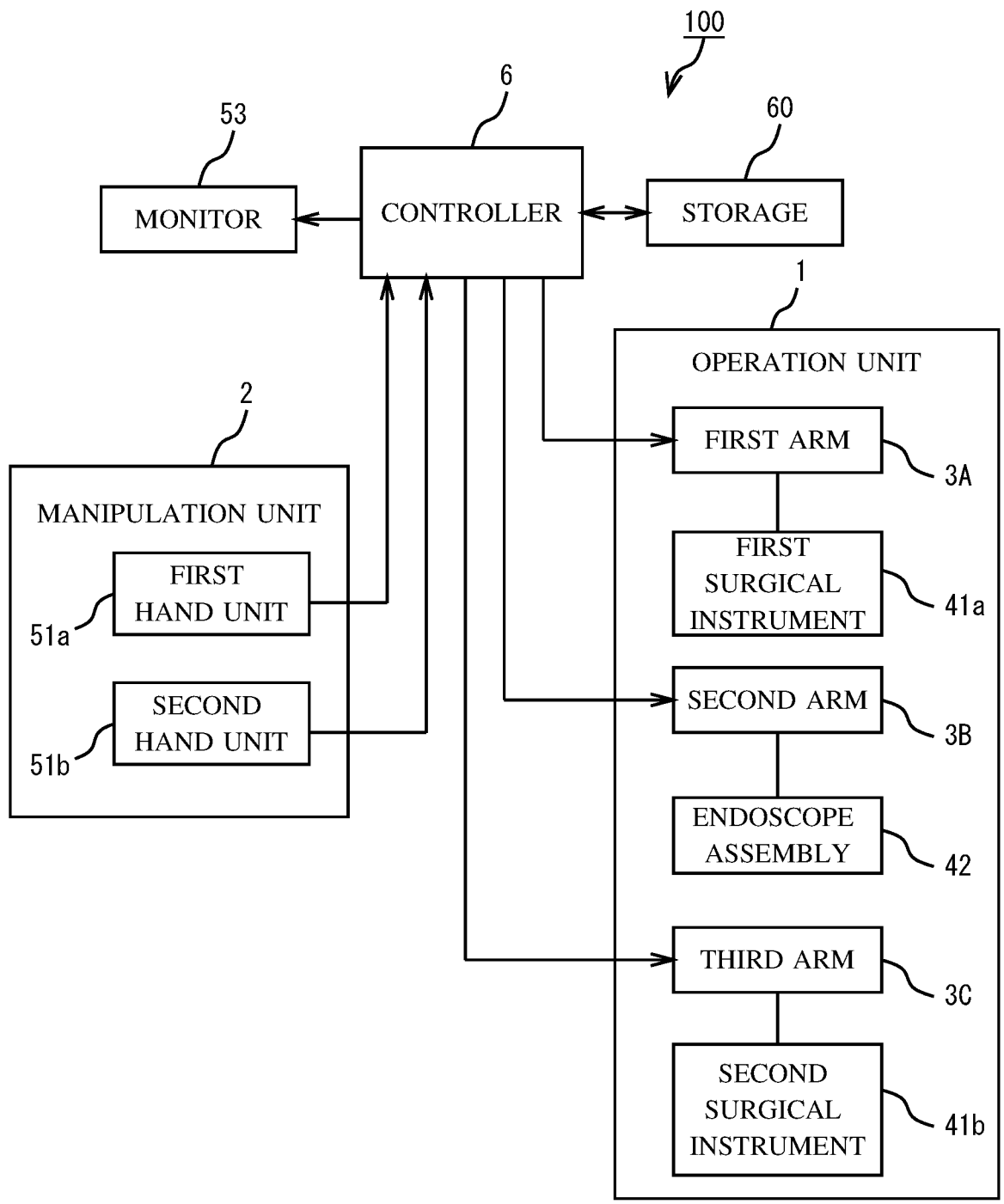
FIG. 2 is a block diagram showing the configuration of a control system of the surgical system shown in FIG. 1.

FIG. 1 is a schematic diagram showing an entire configuration of a surgical system according to one embodiment of the present disclosure. FIG. 2 is a block diagram showing the configuration of a control system of the surgical system shown in FIG. 1. As shown in FIG. 1, a surgical system 100 is a system which performs endoscopic surgery for a patient P by using an operation unit 1 which is operated in such a manner that an operator O, such as a doctor, manipulates a manipulation unit 2 as in robot assisted surgery, robot remote surgery, or the like.

The surgical system 100 includes the operation unit 1 and the manipulation unit 2 that manipulates the operation unit 1. The manipulation unit 2 is arranged away from the operation unit 1, and the operation unit 1 is remotely manipulated by the manipulation unit 2. The operator O inputs to the manipulation unit 2 an operation to be performed by the operation unit 1, and the manipulation unit 2 transmits an operating command of the operation to the operation unit 1. The operation unit 1 receives the operating command transmitted from the manipulation unit 2 and operates an endoscope assembly 42, a surgical instrument 41, and the like included in the operation unit 1 based on the operating command.

The manipulation unit 2 constitutes an interface between the surgical system 100 and the operator O and is an apparatus used to manipulate the operation unit 1. The manipulation unit 2 is arranged adjacent to or away from an operating table 111 inside an operating room or arranged outside the operating room. The manipulation unit 2 includes manipulation inputters, such as a manipulator arm 51 and a manipulation pedal 52, used by the operator O to input the operating command. In the present embodiment, the manipulator arm 51 includes a first hand unit 51a manipulated by the operator O with his/her right hand and a second hand unit 51b manipulated by the operator O with his/her left hand.

The manipulation unit 2 further includes a monitor 53 that displays an image taken by a camera of the endoscope assembly 42. The monitor 53 may be configured as a unit (display unit) arranged separately from the manipulation unit 2 including the manipulation inputters. While visually confirming an affected part on the monitor 53, the operator O manipulates the manipulation inputters to input the operating command to the manipulation unit 2. The operating command input to the manipulation unit 2 is transmitted to a below-described controller 6 of the operation unit 1 through wired communication or wireless communication.

The operation unit 1 constitutes an interface between the surgical system 100 and the patient P. The operation unit 1 is arranged adjacent to the operating table 111 on which the patient P lies inside the operating room. The inside of the operating room is a sterile field.

The operation unit 1 includes a positioner 7, a platform 5 attached to a tip end portion of the positioner 7, and patient-side manipulator arms (hereinafter simply referred to as "arms 3") detachably attached to the platform 5. The positioner 7 is configured as a multiaxial robot and can three-dimensionally move the position of the platform 5 relative to a base 70 placed at a predetermined position of the operating room. The arms 3 and the platform 5 are covered with a sterile drape (not shown) to be shielded from the sterile field in the operating room.

In the operation unit 1, the platform 5 serves as a "hub" for the arms 3. In the present embodiment, the positioner 7 and the platform 5 constitute a manipulator arm support S that supports the arms 3 such that the arms 3 are movable. However, the manipulator arm support S may include at least the platform 5. For example, instead of the positioner 7, the manipulator arm support S may include a linear motion rail or a lifting device or may be configured such that the platform 5 is supported by a bracket attached to a ceiling or a wall.

In the above operation unit 1, components from the positioner 7 to the endoscope assembly 42 or each surgical instrument 41 are coupled to each other in series. In the present description, regarding each of these components, an end portion located closer to the positioner 7 (more specifically, a portion of the positioner 7 which portion contacts a floor of the operating room) is referred to as a "base end portion," and an opposite end portion is referred to as a "tip end portion."

The arms 3 are attachable to and detachable from the platform 5. The arms 3 have water resistance, heat resistance, and chemical resistance for a cleaning treatment and a sterilization treatment. There are various methods as the sterilization treatment of the arms 3. For example, high pressure steam sterilization, EOG sterilization, chemical sterilization using disinfectant, or the like may be selectively used.

Although not shown in detail, each of the arms 3 includes: a base detachably attached to the platform 5; and first to sixth links sequentially coupled to each other from the base toward the tip end portion. The arm 3 is configured as a seven-axis articulated arm including a redundant axis. Therefore, the arm 3 is configured such that the tip end portion thereof is movable relative to the base end portion thereof in a three-dimensional space. Since the arm 3 includes the redundant axis, the posture of the arm can be changed without changing the position of the tip end portion of the arm 3. In the present embodiment, the arms 3 included in the operation unit 1 are the same in configuration as each other or are similar in configuration to each other. However, at least one of the arms 3 may be different in configuration from the other arms.

An outer shell of the arm 3 is mainly formed by a member, such as stainless steel, having heat resistance and chemical resistance. Moreover, a seal (not shown) for obtaining water resistance is provided at a coupler between the links. The seal has heat resistance corresponding to high pressure steam sterilization and chemical resistance with respect to disinfectant. Regarding the coupler between the links, an end portion of one of the links is inserted into an end portion of the other link, and the seal is arranged so as to fill a gap between the end portions of the links, and is therefore hidden in terms of appearance. With this, infiltration of water, chemical liquid, and steam through the gap between the seal and the link is suppressed.

A holder (instrument holder) 36 (see FIGS. 3 and 4 described below) that can hold the below-described surgical instrument 41 or the below-described endoscope assembly 42 are provided at the tip end portion of each arm 3. A translational arm (not shown) may be attached to the tip end portion of the sixth link of the arm 3. In this case, the holder 36 is provided at the tip end portion of the translational arm. With this, when the holder 36 of the translational arm is made to perform a translational movement in a long-axis direction, the surgical instrument 41 or the endoscope assembly 42 attached to the holder 36 can be made to perform a translational movement in the long-axis direction.

As shown in FIG. 2, a first surgical instrument 41a is detachably held by a tip end portion of a first arm 3A that is one of the arms 3. The endoscope assembly 42 is held by a tip end portion of a second arm 3B that is another one of the arms 3. A second surgical instrument 41b is detachably held at a tip end portion of a third arm 3C that is yet another one of the arms 3. Although not shown, the surgical instruments may be detachably held by the other arms 3.

Figure 3:
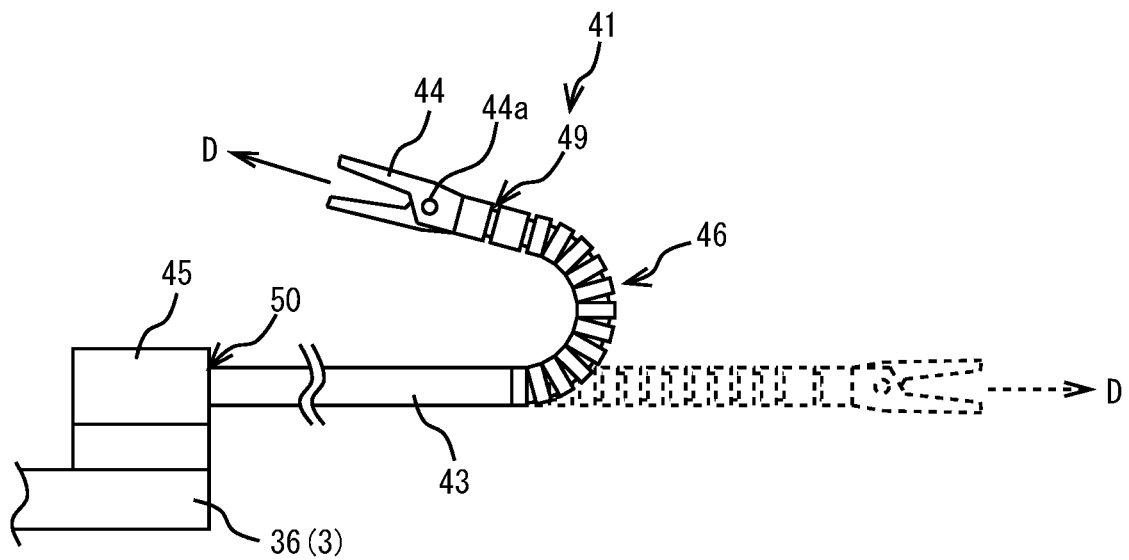
FIG. 3 is a diagram showing one example of a surgical instrument according to the present embodiment.

FIG. 3 is a diagram showing one example of the surgical instrument according to the present embodiment. Each of the surgical instruments 41 (such as the first surgical instrument 41a and the second surgical instrument 41b) includes: a drive unit 45 provided at the base end portion of the surgical instrument 41; an end effector (treatment tool) 44 provided at the tip end portion of the surgical instrument 41; and a thin and long shaft 43 coupling the drive unit 45 and the end effector 44. The base end portion of the surgical instrument 41 is attachable to and detachable from the holder 36 of each arm 3.

A long-axis direction D is defined at the surgical instrument 41. The drive unit 45, the shaft 43, and the end effector 44 are arranged along the long-axis direction D. The end effector 44 of the surgical instrument 41 is selected from the group consisting of tools (such as a pair of forceps, a pair of scissors, a grasper, a needle holder, a microdissector, a staple applier, a tucker, a suction cleaning tool, a snare wire, and a clip applier) each having an operating joint and tools (such as a cutting blade, a cautery probe, a washer, a catheter, and a suction orifice) each not having a joint. FIG. 3 shows a pair of forceps including a pair of open-close claws (gripping pieces).

In the present embodiment, the surgical instrument 41 includes an instrument bendable portion 46 that bends the shaft 43 relative to the long-axis direction D. The instrument bendable portion 46 is bendable in a predetermined plane (bent plane). In the present embodiment, the long-axis direction D when the instrument bendable portion 46 is bent is defined as an extending direction of the shaft 43 including the instrument bendable portion 46. To be specific, the long-axis direction D changes in accordance with the bending of the instrument bendable portion 46.

Moreover, the shaft 43 is rotatable about a long axis relative to a base portion (drive unit 45) of the surgical instrument 41 at a base end portion of the shaft 43 (see a base end-side rotating shaft 50 in FIG. 3). Therefore, since the bent plane rotates about the long axis by the rotation of the shaft 43 about the long axis, a bending direction of the instrument bendable portion 46 can be set three-dimensionally. The bending operation of the instrument bendable portion 46 is realized by a known configuration, such as a hydraulic configuration or a mechanical configuration including wires extending therein.

The surgical instrument 41 further includes a tip end-side rotating shaft 49 at a tip end portion of the shaft 43 (instrument bendable portion 46). With this, the end effector 44 is rotatable about the long axis relative to the shaft 43. Moreover, when the end effector 44 is the forceps unit shown in FIG. 3, the end effector 44 includes a gripping pieces spindle 44a by which tip end portions of the gripping pieces open or close (i.e., by which gripping and releasing are switched). As above, the surgical instrument 41 includes, as moving parts, the base end-side rotating shaft 50, the instrument bendable portion 46, the tip end-side rotating shaft 49, and the gripping pieces spindle 44a.

Figure 4:
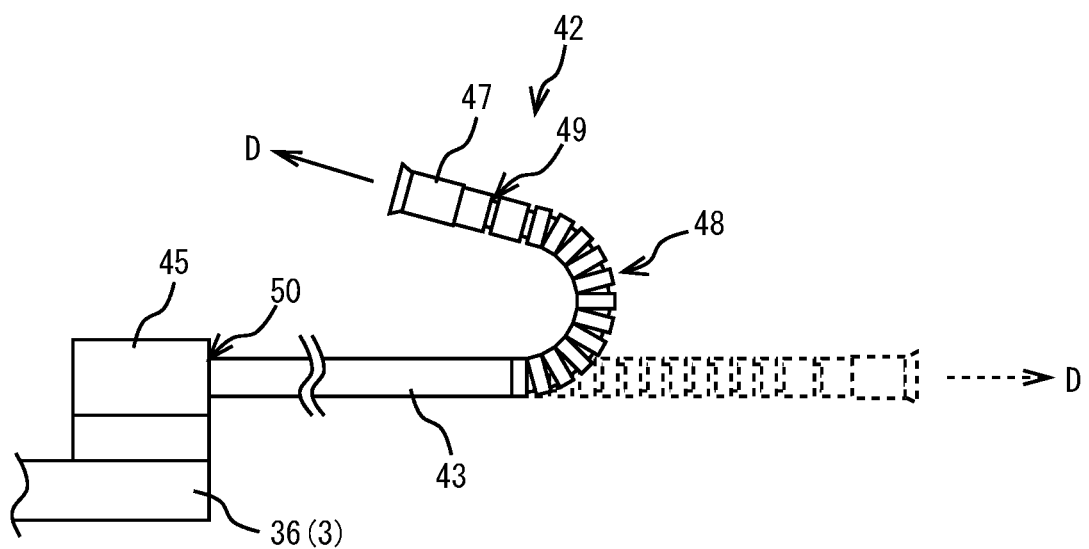
FIG. 4 is a diagram showing one example of an endoscope assembly according to the present embodiment.

FIG. 4 is a diagram showing one example of the endoscope assembly according to the present embodiment. Instead of the end effector 44 of the surgical instrument 41, a camera 47 is attached to a tip end portion of the endoscope assembly 42. Therefore, the endoscope assembly 42 includes the drive unit 45, the base end-side rotating shaft 50, the shaft 43, the tip end-side rotating shaft 49, and the camera 47. An image taken by the camera 47 is displayed on the monitor 53 of the manipulation unit 2. A base end portion of the endoscope assembly 42 is attachable to and detachable from the holder 36 of the arm 3. Instead of this, the endoscope assembly 42 may be undetachably attached to the holder 36 of the arm 3. To be specific, the operation unit 1 may include an arm dedicated for the endoscope assembly 42.

The endoscope assembly 42 includes an endoscope bendable portion 48 that bends the shaft 43 relative to the long-axis direction D. The endoscope bendable portion 48 is similar in configuration to the instrument bendable portion 46 of the surgical instrument 41. In the endoscope assembly 42, the shaft 43 is rotatable about the long axis relative to the base portion (drive unit 45) of the surgical instrument 41 at the base end portion of the shaft 43. Therefore, since the bent plane rotates about the long axis by the rotation of the shaft 43 about the long axis, the bending direction of the endoscope bendable portion 48 can be set three-dimensionally.

The operation unit 1 is controlled by a controller 6. The controller 6 is constituted by a computer, such as a microcontroller. The controller 6 is configured as a processing circuit including a processor, a volatile memory, a non-volatile memory, an I/O interface, and the like.

In surgery performed by using the operation unit 1 configured as above, first, the controller 6 which has received the operating command from the manipulation unit 2 operates the positioner 7 to position the platform 5 such that a predetermined positional relation between the platform 5 and the operating table 111 or between the platform 5 and the patient P is realized. Next, the controller 6 operates the arms 3 to position the endoscope assembly 42 and the surgical instruments 41 such that a predetermined initial positional relation among a sleeve (cannula sleeve) 110 placed on a body surface of the patient P, the endoscope assembly 42, and the surgical instruments 41 is realized. The positioning operation of the positioner 7 and the positioning operations of the arms 3 may be performed at the same time.

With the positioner 7 stopped basically, the controller 6 performs the surgery by operating the surgical instruments 41 by the arms 3 in accordance with the operating command from the manipulation unit 2 while suitably changing the positions and postures of the endoscope assembly 42 and the surgical instruments 41.

The arms 3 are respectively assigned to the first hand unit 51a and the second hand unit 51b of the manipulation unit 2 so as to be manipulated by the first hand unit 51a and the second hand unit 51b. For example, the first arm 3A is assigned to the first hand unit 51a, and the third arm 3C is assigned to the second hand unit 51b. With this, the operating command for the first arm 3A holding the first surgical instrument 41a is generated by a manipulation input to the first hand unit 51a, and the operating command for the third arm 3C holding the second surgical instrument 41b is generated by a manipulation input to the second hand unit 51b.

Each of the arms 3 assigned to the hand units 51a and 51b is selected from the arms 3 by manipulating the manipulation unit 2. To be specific, the arms 3 which operate by manipulating the hand units 51a and 51b can be switched even during the surgery. For example, the arm 3 assigned to the second hand unit 51b in the above example is switched from the third arm 3C to the second arm 3B. With this, the operating command for the second arm 3B holding the endoscope assembly 42 is generated by a manipulation input to the second hand unit 51b.

The operating commands that operate the bendable portion 46 of the surgical instrument 41 and the bendable portion 48 of the endoscope assembly 42 can also be generated by manipulation inputs to the hand units 51a and 51b.

The controller 6 controls the movements of the arms 3 based on the operating commands. The controller 6 controls the rotation of each servomotor (not shown) that drives a shaft of the corresponding arm 3 through an amplifying circuit and the like. A rotation angle of the servomotor is detected by a corresponding encoder, and a drive command value for the servomotor is generated based on the rotation angle and the operating command. Thus, the servomotor is servo-controlled such that the position and posture of the tip end portion of the arm 3 reaches the position and posture that are based on the operating command.

The surgical system 100 includes a storage 60 that stores data readable by the controller 6. The storage 60 prestores surgical information input through the manipulation unit 2. The surgical information contains a combination of the arms 3 to be used in the surgery. Moreover, the storage 60 stores information, such as the length of the surgical instrument (the endoscope assembly 42 or the surgical instrument 41), held by the tip end portion of the arm 3, in the long-axis direction D. With this, the controller 6 can recognize position coordinates of the tip end portions of the surgical instrument 41 and the endoscope assembly 42 held by the tip end portions of the arms 3.

The controller 6 can execute bending following control of controlling the endoscope assembly 42 such that the endoscope assembly 42 is bent to follow the bending of the instrument bendable portion 46 of the surgical instrument 41 which is bent based on the operating command. The manipulation unit 2 is configured to receive a manipulation input by which whether to perform the bending following control is switched.

The following will describe an example in which the bending following control of following the bending of the first surgical instrument 41a is set to be performed by the manipulation input to the manipulation unit 2 from the operator O. In this case, in the subsequent manipulation input, when the operating command for the first surgical instrument 41a contains the bending operation of the instrument bendable portion 46, the controller 6 controls the endoscope assembly 42 such that the endoscope assembly 42 is bent to follow the bending of the first surgical instrument 41a.

Therefore, the direction of the image taken by the camera 47 of the endoscope assembly 42 can be easily adjusted in accordance with the movement of the tip end portion of the first surgical instrument 41a to a direction in which the tip end portion of the first surgical instrument 41a is directed. Thus, even when the first surgical instrument 41a is bent, the image of the tip end portion of the first surgical instrument 41a can be easily acquired. The following will describe a specific example of the bending following control.

First Control Mode

In a first control mode, the controller 6 determines a bending angle $\theta_C$ of the endoscope bendable portion 48 of the endoscope assembly 42 in accordance with a bending angle $\theta_H$ of the instrument bendable portion 46 of the first surgical instrument 41a. For example, when the bending angle $\theta_C$ is equal to the bending angle $\theta_H$, the controller 6 controls the second arm 3B and the endoscope assembly 42 such that the endoscope bendable portion 48 is bent at a bending angle that is equal to the bending angle $\theta_H$ of the instrument bendable portion 46 of the first surgical instrument 41a.

A relation between the bending angle $\theta_H$ of the instrument bendable portion 46 and the bending angle $\theta_C$ of the endoscope bendable portion 48 is not limited to the above relation. For example, the bending angle $\theta_C$ may be set to be smaller than the bending angle $\theta_H$ of the instrument bendable portion 46 ($\theta_C < \theta_H$; for example, $\theta_C = \theta_H/2$). Moreover, the bending angle $\theta_C$ may be set to be larger than the bending angle $\theta_H$ of the instrument bendable portion 46 ($\theta_C > \theta_H$; for example, $\theta_C = 2\theta_H$). Furthermore, the relation between the bending angle $\theta_H$ of the instrument bendable portion 46 and the bending angle $\theta_C$ of the endoscope bendable portion 48 may change in accordance with the bending angle $\theta_H$ of the instrument bendable portion 46. For example, when the bending angle $\theta_C$ is equal to the bending angle $k\theta_H$, a coefficient k by which the bending angle $\theta_C$ of the endoscope bendable portion 48 is multiplied may increase (or decrease) as the bending angle $\theta_H$ of the instrument bendable portion 46 increases.

According to this mode, the bending of the endoscope assembly 42 can be made to follow the bending of the first surgical instrument 41a by simple control.

As described above, the endoscope assembly 42 and the second arm 3B holding the endoscope assembly 42 can operate based on the manipulation of the operator O by setting the second arm 3B as a target to be manipulated by the first hand unit 51a or the second hand unit 51b. Therefore, the position and posture of the endoscope assembly 42 can be adjusted based on the manipulation of the operator O such that after the bending operation of the endoscope assembly 42 is performed so as to follow the bending of the first surgical instrument 41a, an image region more desirable for the operator O is displayed on the monitor 53. As above, even when the position and posture of the endoscope assembly 42 are adjusted by manipulating the manipulation unit 2 after the execution of the bending following control, the amount of adjustment by the manipulation of the operator O can be made small by executing the bending following control of the endoscope assembly 42 in advance.

Second Control Mode

In a second control mode, the controller 6 performs first calculation processing of determining the position and posture of the endoscope assembly 42 such that when the first surgical instrument 41*a* is bent, a relative relation between the position and posture of the tip end portion of the first surgical instrument 41*a* before the instrument bendable portion 46 is bent and the position and posture of the tip end portion of the endoscope assembly 42 before the endoscope bendable portion 48 is bent is maintained.

Therefore, the storage 60 stores the position and posture of the tip end portion of the first surgical instrument 41*a* before the instrument bendable portion 46 is bent and the position and posture of the tip end portion of the endoscope assembly 42 before the endoscope bendable portion 48 is bent.

Figure 5:
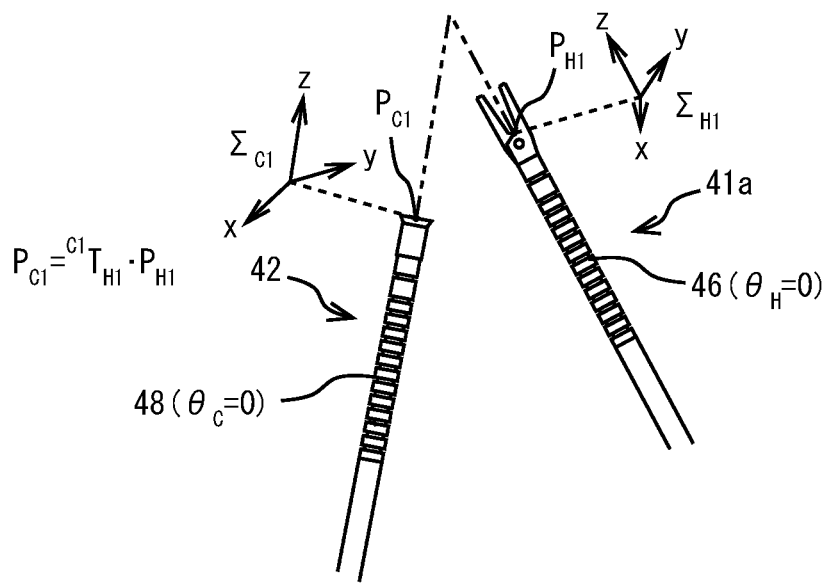
FIG. 5 is a partially enlarged view showing a first surgical instrument and the endoscope assembly before the first surgical instrument and the endoscope assembly are bent in a second control mode of the present embodiment.
Figure 6:
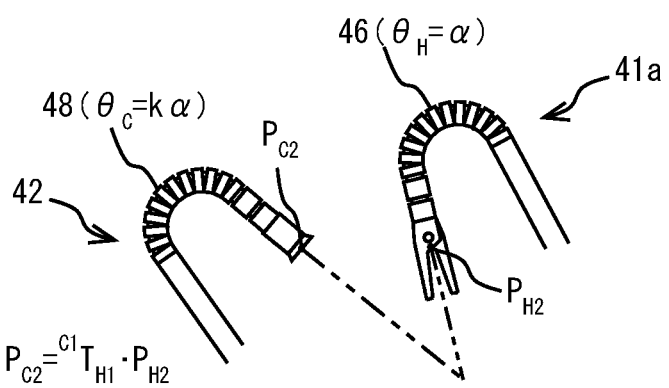
FIG. 6 is a partially enlarged view showing the first surgical instrument and the endoscope assembly after the endoscope assembly has followed a bending operation of the first surgical instrument in the second control mode of the present embodiment.

FIG. 5 is a partially enlarged view showing the first surgical instrument and the endoscope assembly before the first surgical instrument and the endoscope assembly are bent in the second control mode of the present embodiment. FIG. 6 is a partially enlarged view showing the first surgical instrument and the endoscope assembly after the endoscope assembly has followed the bending operation of the first surgical instrument in the second control mode of the present embodiment. In the example shown in FIG. 5, both the bending angle $\theta_H$ of the instrument bendable portion 46 of the first surgical instrument 41*a* and the bending angle $\theta_C$ of the endoscope bendable portion 48 of the endoscope assembly 42 are zero.

A coordinate system (first surgical instrument coordinate system) of the tip end portion of the first surgical instrument 41*a* is represented by $\Sigma_{H1}$, and a coordinate system (endoscope assembly coordinate system) of the tip end portion of the endoscope assembly 42 is represented by $\Sigma_{C1}$. At this time, a relative relation between a matrix $P_{C1}$ indicating the position and posture of the endoscope assembly coordinate system $\Sigma_{C1}$ of the tip end portion of the endoscope assembly 42 before the bending and a matrix $P_{H1}$ indicating the position and posture of the first surgical instrument coordinate system $\Sigma_{H1}$ of the tip end portion of the first surgical instrument 41*a* before the bending is represented by Formula (1) below. Herein, $^{C1}T_{H1}$ indicates a homogeneous transformation matrix when the position and posture of the first surgical instrument coordinate system $\Sigma_{H1}$ are viewed from the endoscope assembly coordinate system $\Sigma_{C1}$.

Formula 1

$$P_{C1} = {}^{C1}T_{H1} \cdot P_1 \quad (1)$$

The homogeneous transformation matrix $^{C1}T_{H1}$ is represented as below by using: the position coordinate (X, Y, Z) of the tip end portion of the first surgical instrument 41*a* in the endoscope assembly coordinate system $\Sigma_{C1}$; an x-axis unit vector component $(n_x, n_y, n_z)$ of the first surgical instrument coordinate system $\Sigma_{H1}$ when viewed from the endoscope assembly coordinate system $\Sigma_{C1}$; a y-axis unit vector component $(o_x, o_y, o_z)$ of the first surgical instrument coordinate system $\Sigma_{H1}$ when viewed from the endoscope assembly coordinate system $\Sigma_{C1}$; and a z-axis unit vector component $(a_x, a_y, a_z)$ of the first surgical instrument coordinate system $\Sigma_{H1}$ when viewed from the endoscope assembly coordinate system $\Sigma_{C1}$.

Formula 2

$$
{}^{C1}T_{H1} = \begin{bmatrix} n_x & o_x & a_x & X \\ n_y & o_y & a_y & Y \\ n_z & o_z & a_x & Z \\ 0 & 0 & 0 & 1 \end{bmatrix} \quad (2)
$$

In Formula (2) above, the unit vector component (3×3 matrix represented by $n_i, o_i, a_i$ (i denotes x, y, or z)) of each axis of the first surgical instrument coordinate system $\Sigma_{H1}$ when viewed from the endoscope assembly coordinate system $\Sigma_{C1}$ indicates the posture of the tip end portion of the first surgical instrument 41*a* when viewed from the tip end portion of the endoscope assembly 42.

The storage 60 stores the homogeneous transformation matrix $^{C1}T_{H1}$ as the above relative relation. Then, when the operating command containing the bending operation of bending the instrument bendable portion 46 has been generated as the operating command for the first surgical instrument 41*a*, the controller 6 calculates a matrix $P_{C2}$ indicating the position and posture of the tip end portion of the endoscope assembly 42 which follows the movement of the first surgical instrument 41*a*, by using a matrix $P_{H2}$ indicating the position and posture of the tip end portion of the first surgical instrument 41*a* at the time of the bending and the above homogeneous transformation matrix $^{C1}T_{H1}$.

Formula 3

$$P_{C2} = {}^{C1}T_{H1} \cdot P_{H2} \quad (3)$$

The controller 6 calculates and obtains, by inverse transformation, the bending angle $\theta_C$ of the endoscope bendable portion 48 of the endoscope assembly 42 and the position and posture (displacement magnitude of each joint shaft of the second arm 3B) of the second arm 3B holding the endoscope assembly 42 such that the position and posture of the tip end portion of the endoscope assembly 42 become the position and posture represented by the matrix $P_{C2}$ indicating the calculated position and posture.

For example, the controller 6 may perform the first calculation processing based on a constraint condition that the bending angle $\theta_C(=k\alpha)$ of the endoscope bendable portion 48 of the endoscope assembly 42 corresponds to the bending angle $\theta_H(=\alpha)$ of the instrument bendable portion 46 of the first surgical instrument 41*a* after the bending operation. With this, the calculation of the position and posture of the endoscope assembly 42 that is assumed to be bent can be performed, and the amount of calculation can be reduced.

After the above calculation, the controller 6 controls the bending operation of the endoscope bendable portion 48 of the endoscope assembly 42 and the operation of the second arm 3B based on the calculation result. As a result, as shown in FIG. 6, the endoscope assembly 42 is subjected to the bending following control such that the relative relation between the position and posture of the tip end portion of the first surgical instrument 41*a* and the position and posture of the tip end portion of the endoscope assembly 42 is maintained before and after the bending operation of the first surgical instrument 41*a*.

According to the second control mode in which the first calculation processing is used, the bending operation of the first surgical instrument 41*a* and the bending operation of the endoscope assembly 42 are performed in a state where the relative relation between the position and posture of the tip end portion of the first surgical instrument 41*a* and the position and posture of the tip end portion of the endoscope assembly 42 is maintained. Therefore, the image region taken by the camera 47 of the endoscope assembly 42 for the tip end portion of the first surgical instrument 41*a* is maintained before and after the bending.

In the second control mode, after the endoscope assembly 42 is operated so as to follow the bending of the first surgical instrument 41*a*, the position and posture of the endoscope assembly 42 can be adjusted based on the manipulation of the operator O such that the image region more desirable for the operator O is displayed on the monitor 53. According to the second control mode, the amount of adjustment of the endoscope assembly 42 by the manipulation of the operator O after the bending operation of the first surgical instrument 41*a* can be made smaller.

In some cases, the position of the endoscope assembly 42 cannot be determined in the above first calculation processing such that the above relative relation is maintained. For example, the position of the endoscope assembly 42 cannot be determined when there are plural combinations of the bending angle θc of the endoscope bendable portion 48 and the position and posture of the second arm 3B corresponding to the matrix $P_{c2}$ indicating the position and posture after the bending following operation (i.e., when there are plural solutions). Moreover, there may be, for example, a case where the tip end portion of the endoscope assembly 42 cannot reach a position where the tip end portion of the endoscope assembly 42 should reach after the bending following operation, due to other constraint conditions, such as restriction of a moving range of the second arm 3B, interference with other arms, and the position of the sleeve 110 (a position through which the shaft 43 of the endoscope assembly 42 has to pass) (i.e., a case where there is no solution).

In such a case, the controller 6 may determine the posture of the tip end portion of the endoscope assembly 42 such that a relation between the posture of the tip end portion of the first surgical instrument 41*a* before the instrument bendable portion 46 is bent and the posture of the tip end portion of the endoscope assembly 42 before the endoscope bendable portion 48 is bent is maintained. In this case, the bending angle $\theta_C$ of the endoscope bendable portion 48 of the endoscope assembly 42 and the position of the second arm 3B may be controlled such that the relation between those postures is maintained.

According to this, even when the relative relation between the position and posture of the tip end portion of the first surgical instrument 41*a* and the position and posture of the tip end portion of the endoscope assembly 42 cannot be maintained, the controller 6 operates such that the relation between the posture of the tip end portion of the first surgical instrument 41*a* and the posture of the tip end portion of the endoscope assembly 42 is maintained. Therefore, the endoscope assembly 42 can be made to follow the bending operation of the first surgical instrument 41*a* as much as possible.

Instead of this, when the position of the endoscope assembly 42 cannot be determined in the first calculation processing such that the above relative relation is maintained, the bending angle $\theta_C$ of the endoscope bendable portion 48 of the endoscope assembly 42 may be determined in accordance with the bending angle $\theta_H$ of the instrument bendable portion 46 of the first surgical instrument 41*a*. To be specific, when the controller 6 cannot determine the solution of the first calculation processing in the second control mode, the controller 6 may switch to the first control mode.

According to this, even when the relative relation between the position and posture of the tip end portion of the first surgical instrument 41*a* and the position and posture of the tip end portion of the endoscope assembly 42 cannot be maintained, the bending angle $\theta_C$ of the endoscope bendable portion 48 of the endoscope assembly 42 is determined in accordance with the bending angle $\theta_H$ of the instrument bendable portion 46 of the first surgical instrument 41*a*. Therefore, the endoscope assembly 42 can be made to follow the bending operation of the first surgical instrument 41*a* as much as possible.

The above example has described a case where the endoscope assembly 42 (and the second arm 3B) operates so as to follow the bending operation of the first surgical instrument 41*a* held by the first arm 3A. However, the endoscope assembly 42 (and the second arm 3B) may be able to operate so as to follow the bending operation of the surgical instrument 41 held by the arm 3 other than the first arm 3A. For example, the endoscope assembly 42 (and the second arm 3B) may be able to operate so as to follow the bending operation of the second surgical instrument 41*b* held by the third arm 3C. To be specific, the surgical instrument that the endoscope assembly 42 follows may be selectable from the first surgical instrument 41*a* and the second surgical instrument 41*b*.

For example, a changing-over switch (not shown) for the bending following control may be provided at the manipulation unit 2. The changing-over switch may switch among following the arm 3 assigned to the first hand unit 51*a*, following the arm 3 assigned to the second hand unit 51*b*, and non-following. When the non-following is selected by the changing-over switch, and the first surgical instrument 41*a* or the second surgical instrument 41*b* performs the bending operation, the endoscope bendable portion 48 of the endoscope assembly 42 does not follow the bending operation. However, even in this case, when the second arm 3B holding the endoscope assembly 42 is assigned to the hand unit 51*a* or 51*b*, the endoscope assembly 42 can be made to independently perform the bending operation by manipulating the hand unit 51*a* or 51*b*.

When the hand unit 51*a* or 51*b* is selected by the changing-over switch as a target to be followed, and the arm 3 assigned to the selected hand unit 51*a* or 51*b* is the surgical instrument 41*a* or 41*b* including the instrument bendable portion 46, the controller 6 controls the endoscope assembly 42 and the second arm 3B such that the endoscope assembly 42 and the second arm 3B follow the bending operation of the surgical instrument 41*a* or 41*b*.

When (i) the first arm 3A holding the first surgical instrument 41*a* is assigned to one of the hand units (for example, the first hand unit 51*a*), (ii) the first hand unit 51*a* is selected by the changing-over switch as the target to be followed, and (iii) the second arm 3B holding the endoscope assembly 42 is assigned to the other hand unit (for example, the second hand unit 51*b*), the controller 6 may perform a control operation of not performing the bending following control for the endoscope assembly 42 and the second arm 3B (automatically cancel the following) regardless of the bending operation of the instrument bendable portion 46 of the first surgical instrument 41*a*. Instead of this, even when the second arm 3B holding the endoscope assembly 42 is assigned to the hand unit 51*a* or 51*b*, the controller 6 may execute the bending following control.

Moreover, the controller 6 may be able to set the surgical instrument 41a or 41b as a target to be followed by the endoscope assembly 42, by the manipulation of the manipulation unit 2 regardless of the assignment of the hand units 51a and 51b.

According to this configuration, when the surgical instruments 41a and 41b are respectively held by the arms 3A and 3C, the target to be followed in the bending following control of the endoscope assembly 42 and the second arm 3B can be switched. With this, when there are the plural arms 3A and 3B to which the surgical instruments 41a and 41b are attached, an image of a part that the operator O wants to see can be easily acquired.

From the foregoing explanation, many modifications and other embodiments of the present disclosure are obvious to one skilled in the art. Therefore, the foregoing explanation should be interpreted only as an example and is provided for the purpose of teaching the best mode for carrying out the present disclosure to one skilled in the art. The structures and/or functional details may be substantially modified within the scope of the present disclosure.

INDUSTRIAL APPLICABILITY

The method of controlling the surgical system and the surgical system according to the present disclosure are useful to easily acquire an image of a tip end portion of a surgical instrument attached to a manipulator arm even when the surgical instrument is bent.

The invention claimed is:

1. A method of controlling a surgical system,
the surgical system comprising:
manipulator arms including respective instrument holders at tip end portions of the manipulator arms, the instrument holders holding respective long-axis surgical instruments, the tip end portions of the manipulator arms being three-dimensionally movable relative to corresponding base end portions of the manipulator arms;
a manipulation unit that generates, based on a manipulation input, an operating command that moves the manipulator arms; and
a controller that controls movements of the manipulator arms based on the operating command, wherein
the manipulator arms include
a first manipulator arm including the instrument holder holding a first surgical instrument including an instrument bendable portion and
a second manipulator arm including the instrument holder holding an endoscope assembly including an endoscope bendable portion and a camera at a tip end portion of the endoscope assembly,
the method comprising controlling the endoscope assembly such that the endoscope assembly is bent so as to follow bending of the first surgical instrument that is bent based on the operating command.

2. The method according to claim 1, comprising determining a bending angle of the endoscope bendable portion of the endoscope assembly in accordance with a bending angle of the instrument bendable portion of the first surgical instrument.

3. The method according to claim 1, wherein:
the surgical system includes a storage that stores data readable by the controller; and
the storage stores a position and posture of a tip end portion of the first surgical instrument before the instrument bendable portion is bent and a position and posture of the tip end portion of the endoscope assembly before the endoscope bendable portion is bent,
the method comprising performing, when the first surgical instrument is bent, first calculation processing of determining the position and posture of the endoscope assembly such that a relative relation between the position and posture of the tip end portion of the first surgical instrument before the instrument bendable portion is bent and the position and posture of the tip end portion of the endoscope assembly before the endoscope bendable portion is bent is maintained.

4. The method according to claim 3, comprising, when the position of the endoscope assembly is undeterminable in the first calculation processing such that the relative relation is maintained, determining the posture of the tip end portion of the endoscope assembly such that a relation between the posture of the tip end portion of the first surgical instrument before the instrument bendable portion is bent and the posture of the tip end portion of the endoscope assembly before the endoscope bendable portion is bent is maintained.

5. The method according to claim 3, comprising, when the position of the endoscope assembly is undeterminable in the first calculation processing such that the relative relation is maintained, determining a bending angle of the endoscope bendable portion of the endoscope assembly in accordance with a bending angle of the instrument bendable portion of the first surgical instrument.

6. The method according to claim 3, wherein the first calculation processing is performed based on a constraint condition that the bending angle of the endoscope bendable portion of the endoscope assembly corresponds to the bending angle of the instrument bendable portion of the first surgical instrument.

7. The method according to claim 1, wherein:
the manipulator arms include a third manipulator arm including the instrument holder holding a second surgical instrument including an instrument bendable portion;
in the method, the endoscope assembly is bendable so as to follow bending of the second surgical instrument that is bent based on the operating command; and
a surgical instrument to be followed by the endoscope assembly is selectable from the first surgical instrument and the second surgical instrument.

8. A surgical system comprising:
manipulator arms including respective instrument holders at tip end portions of the manipulator arms, the instrument holders holding respective long-axis surgical instruments, the tip end portions of the manipulator arms being three-dimensionally movable relative to corresponding base end portions of the manipulator arms;
a manipulation unit that generates, based on a manipulation input, an operating command that moves the manipulator arms; and
a controller that controls movements of the manipulator arms based on the operating command, wherein:
the manipulator arms include
a first manipulator arm including the instrument holder holding a first surgical instrument including an instrument bendable portion and
a second manipulator arm including the instrument holder holding an endoscope assembly including an endoscope bendable portion and a camera at a tip end portion of the endoscope assembly; and the controller controls the endoscope assembly such that the endoscope assembly is bent so as to follow bending of the first surgical instrument that is bent based on the operating command.

9. The surgical system according to claim 8, wherein the controller determines a bending angle of the endoscope bendable portion of the endoscope assembly in accordance with a bending angle of the instrument bendable portion of the first surgical instrument.

10. The surgical system according to claim 8, further comprising a storage that stores data readable by the controller, wherein:
the storage stores a position and posture of a tip end portion of the first surgical instrument before the instrument bendable portion is bent and a position and posture of the tip end portion of the endoscope assembly before the endoscope bendable portion is bent; and
the controller performs, when the first surgical instrument is bent, first calculation processing of determining the position and posture of the endoscope assembly such that a relative relation between the position and posture of the tip end portion of the first surgical instrument before the instrument bendable portion is bent and the position and posture of the tip end portion of the endoscope assembly before the endoscope bendable portion is bent is maintained.

11. The surgical system according to claim 10, wherein when the position of the endoscope assembly is undeterminable in the first calculation processing such that the relative relation is maintained, the controller determines the posture of the tip end portion of the endoscope assembly such that a relation between the posture of the tip end portion of the first surgical instrument before the instrument bendable portion is bent and the posture of the tip end portion of the endoscope assembly before the endoscope bendable portion is bent is maintained.

12. The surgical system according to claim 10, wherein when the position of the endoscope assembly is undeterminable in the first calculation processing such that the relative relation is maintained, the controller determines a bending angle of the endoscope bendable portion of the endoscope assembly in accordance with a bending angle of the instrument bendable portion of the first surgical instrument.

13. The surgical system according to claim 10, wherein the controller performs the first calculation processing based on a constraint condition that the bending angle of the endoscope bendable portion of the endoscope assembly corresponds to the bending angle of the instrument bendable portion of the first surgical instrument.

14. The surgical system according to claim 8, wherein:
the manipulator arms include a third manipulator arm including the instrument holder holding a second surgical instrument including an instrument bendable portion;
the surgical system switches between a case where the controller controls the endoscope assembly such that the endoscope assembly is bent so as to follow bending of the first surgical instrument that is bent based on the operating command and a case where the controller controls the endoscope assembly such that the endoscope assembly is bent so as to follow bending of the second surgical instrument that is bent based on the operating command; and
a surgical instrument to be followed by the endoscope assembly is selectable from the first surgical instrument and the second surgical instrument.

* * * * *